Figure 1:
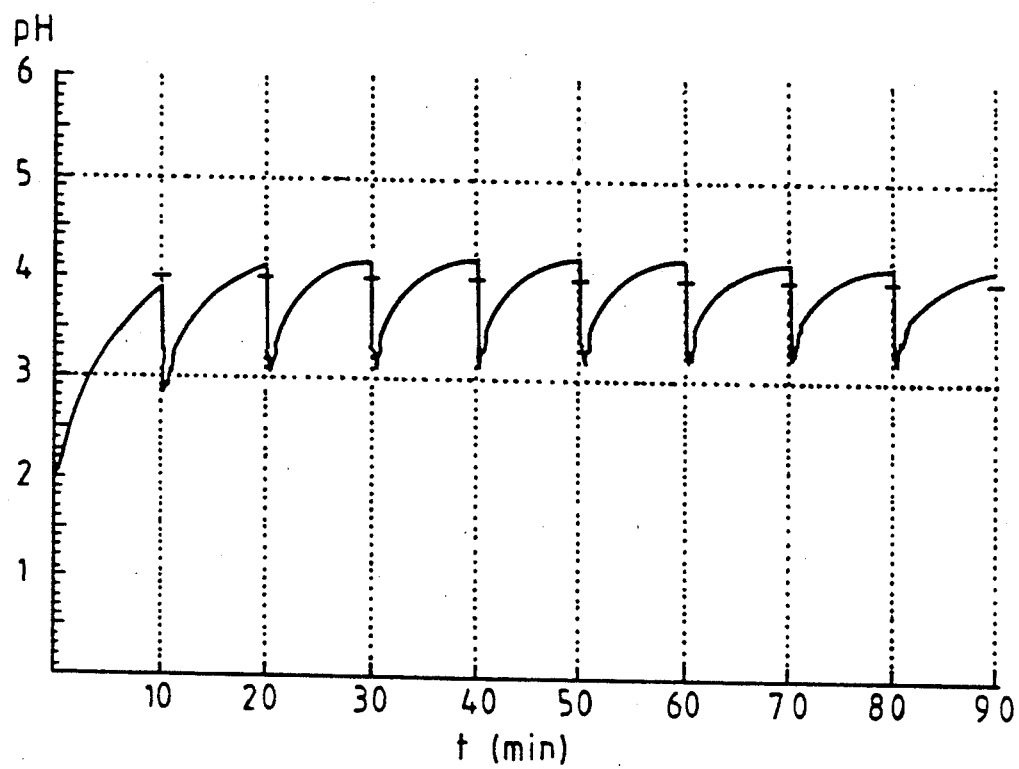

United States Patent [19]
Fritsch et al.

[11] Patent Number: 5,213,794
[45] Date of Patent: May 25, 1993

[54] ANTACID PREPARATION HAVING A PROLONGED GASTRIC RESIDENCE TIME

[75] Inventors: Christian Fritsch, Erlangen; Franz Häusler, Bergisch Gladbach; Jürgen Seedig, Leverkusen, all of Fed. Rep. of Germany

[73] Assignee: Bayer Aktiengesellschaft, Leverkusen, Fed. Rep. of Germany

[21] Appl. No.: 791,944

[22] Filed: Nov. 13, 1991

[30] Foreign Application Priority Data

Nov. 17, 1990 [DE] Fed. Rep. of Germany ....... 4036757

[51] Int. Cl.$^5$ .................... A61K 31/74; A61K 9/36; A61K 9/32; A61K 33/06; A61K 33/14; A61K 33/08
[52] U.S. Cl. ................... 424/78.01; 424/480; 424/482; 424/682; 424/690; 424/692; 514/819
[58] Field of Search ............... 424/480, 482, 682, 690, 424/692, 78.01; 514/819, 820

[56] References Cited

U.S. PATENT DOCUMENTS

| | | | |
|---|---|---|---|
| 3,555,151 | 12/1966 | Kaplan et al. | 424/686 |
| 4,514,389 | 4/1985 | Miyata | 424/690 |
| 4,542,019 | 9/1985 | Lezdey | 424/690 |
| 4,615,697 | 10/1987 | Robinson | 424/425 |
| 4,980,175 | 12/1990 | Chavkin et al. | 424/682 |

FOREIGN PATENT DOCUMENTS 8800051 1/1988 World Int. Prop. O. .
9007344 7/1990 World Int. Prop. O. .

OTHER PUBLICATIONS

Asher Winkelstein, M.D., Effect of Calcium Polycarbophil (Carbofil) Suspension on Gastrointestinal Transit Time, vol. 6, No. 9, Sep. 1964.
Jian-Mei Gu, Binding of Arcylic Polymers to Mucin-/Epithelial Surface-Property Relationships, vol. 5, Issue 1 (1988).
Sau-Hung Spence Leung, The Contribution of Anionic Polymer Structural Features to Mucoadhesion, (1988).

Primary Examiner—Frederick E. Waddell
Assistant Examiner—K. Weddington
Attorney, Agent, or Firm—Sprung Horn Kramer & Woods

[57] ABSTRACT

The present invention relates to an antacid preparation having a prolonged gastric residence time, comprising an antacid active substance, calcium polycarbophil and a water-insoluble, anionic polymer.

9 Claims, 1 Drawing Sheet

ANTACID PREPARATION HAVING A PROLONGED GASTRIC RESIDENCE TIME

The present invention relates to an antacid preparation having a prolonged gastric residence time, comprising an antacid active substance, calcium polycarbophil and a water-insoluble, anionic polymer.

Antacids are widely used in the treatment of various gastric and duodenal disorders and complaints such as gastritis, irritable stomach, heartburn, reflux, reflux oesophagitis, gastric and duodenal ulcers and nightly acid pain.

Antacids used today are mainly aluminum hydroxides and carbonates and magnesium hydroxides and carbonates in different mixture ratios. The two hydroxides (or carbonates) can be combined with one another in the form of physical mixtures, dry gels (for example codried gels), wet gels or alternatively so-called layer lattice antacids. In addition—with less significance—aluminum phosphate, magnesium trisilicate and calcium carbonate are also employed.

The activity of the, antacids is based primarily on their ability to neutralize gastric acid. In addition, however, other mechanisms of action, such as the binding of pepsin and bile acids and the stimulation of sodium bicarbonate secretion in the gastric mucosa by activation of prostaglandin synthesis are also known. Since antacids display their therapeutic action exclusively in the interior of the stomach, the duration of their action is very strongly dependent on the emptying rate of the stomach. It has long been known that the residence time of antacids in the stomach is very short. Literature citations vary between figures of a few minutes up to about an hour. The empty stomach particularly, as it is, for example, at night, empties antacids very rapidly. The capacity to neutralize acid (acid neutralization capacity, ANC) in the commercial antacid preparations is in the range from 10 to 75 mval per single dose. In contrast, patients, depending on the time, age and disease pattern, produce in the range from 0 to 17 mval of gastric acid per hour. Only in those persons having symptoms which accompany a strongly increased secretion of gastric acid, such as, for example, duodenal ulcer patients, are more than 25 mval per hour found. From this comparative analysis, it follows that antacids as a rule are always only able very briefly and frequently incompletely to fulfill their function of neutralizing gastric acid. Often, the acid neutralization capacity of the preparation in the stomach is not used at all. As a result of their brief gastric passage, antacids, given shortly before going to bed, are not able to affect the acid pain which occurs nightly, as they have already been emptied from the stomach at the time that the pain occurs.

On the other hand, another group of gastric therapeutics, the H2 antagonists, are capable of blocking the acid production of the stomach over a period of several hours. In the case of these medicaments, however, not least because of the fact that, as opposed to the antacids, they are distributed in the entire body via the blood, the risk of comparatively serious side effects has to be taken into account, such as, for example, changes in the blood and liver values, states of confusion and the elevation of the prolactin level. H2 antagonists are therefore not generally able to replace the low side-effect antacids in their wide application.

In the past, attempts to prolong the stomach residence time of antacids have not been lacking.

Thus, for example, various gels and tablets were developed which should stay longer in the stomach as a result of their capacity to float.

A floating formulation of this type, containing sodium hydrogen carbonate, calcium carbonate and sodium alginate, is described in Patent Application GB 1,524,740. This medicament preparation produces, with the formation of a calcium alginate gel structure which is given buoyancy as a result of included carbon dioxide gas, a floatable gel (raft) as soon as it comes into contact with the gastric juice. It has been shown that some disadvantages are associated with this formulation. Thus, the principle of flotation is suitable in the case of antacids in particular for the treatment of ascending gastric acid (reflux), but not for the neutralization of the acid in lower sections of the stomach, such as, for example, the antrum. Floating antacids can therefore not act optimally in the many gastric and small intestinal disorders. Moreover, the floating effect always fails if the patient lies on the left side. It has also been found that the acid-binding properties of aluminum-containing antacids are reduced in the floating gel structure and the structural properties are impaired under the influence of aluminum.

Patent Application EP 0,286,085 describes an improved floating gel, in which sodium alginate, for example, is replaced by sodium pectinate. By this means, the last-mentioned disadvantages can be eliminated. The restricted manner of use (reflux) and the failure of the principle in patients lying on the left side, however, remain.

Antacid tablets have also been described which, owing to their property to float in gastric juice, should have a prolonged duration of action. German Offenlegungsschrift 2,611,041 describes a two-layer tablet in which one layer was formulated in sustained release form with floating properties and the other layer in non-sustained release form. The sustained release layer forms a compact methylcellulose gel structure in the gastric juice, which, however, is not capable of being distributed over large parts of the gastric wall and thus of neutralizing acid in a large area. As this formulation can only neutralize at a slow rate in a very limited radius of action, it is not suitable as an antacid.

A completely different route for the preparation of a long-acting antacid is described in PCT Application WO 86/06,632. It is proposed to incorporate antacids in biscuits with the addition of prostaglandin precursors (for example lecithin) and ballast substances. As an additional multiplicity of ingredients, such as are customary in the production of bakery products, is added and a baking process at high temperatures is also proposed, application of this technology for medicaments remains out of the question.

Formulations have also been described which should stay longer in the stomach owing to the swelling and adhesive properties of the polymer substances used. In the case of this procedure, it is to be taken in account that the antacid is not prevented from its reaction with gastric acid too much by inclusion in a swollen matrix. The adhesive properties of the polymers used moreover have to be checked, how far they lead to a good adhesion, especially to mucosa (bioadhesive and mucoadhesive properties). US Patent 3,555,151 describes rapidly disintegrating antacid tablets, comprising strongly swelling and adhesive granules, in which the antacid is included in locust bean flour. As in general swollen highly viscous structures do not have a prolonged gastric residence time as long as they do not have such a large expansion that they fill the whole stomach, it is not possible to start from the fact that the amounts of swelling substance proposed, for example, can achieve the desired effect. In the invention, the adhesive properties of the formulations to the wall of a vessel are described, but not those to the stomach wall.

By means of swelling or adhesive formulations, it has also been attempted in PCT Application WO 88/00,051 to prepare antacids having a prolonged gastric residence time. The anionic polymers used swell strongly at pH values above 6 and form a viscous material in which the antacid is included. In this invention, it was not taken into account that, in the optimum pH range, 3 to 5, which should be achieved in the stomach by administration of antacids, the swelling effect does not occur at all. It was also not possible to produce any evidence that the swollen polymers, be it by their viscous behaviour alone or by specific adhesive properties to the stomach wall, are able to keep back the antacid in the stomach for a longer time. The reaction rate of the formulations with hydrochloric acid was strongly retarded.

It has been disclosed by U.S. Pat. No. 4,615,697 that special polymers, such as the water-insoluble, crosslinked polyacrylic acids (example: polycarbophil) are capable as a result of pronounced bioadhesive properties of prolonging, for example, the gastric residence time of medicaments. Improved absorption behaviour of some pharmaceuticals, such as, for example, hydrochlorothiazide, can result from this. The possibility of achieving a prolongation of the gastric residence time of antacids by means of these polymers was not taken into account. The reason for this omission of the antacids could be the acidic character of the polyacrylic acid derivatives used, since as a result of this there is a restriction of the activity of antacids. Moreover, it was later found by various authors that polycarbophil is not able or only inadequately able to prolong the gastric residence time of pharmaceuticals.

The examples mentioned show that hitherto it has only been possible in an imperfect manner to prepare antacid preparations which fulfill the following requirements:

prolonged residence time, which is also ensured in the living organism;
distribution over a large area in the stomach, i.e. not only local display of the action;
pharmaceutical formulation in the customary sense, i.e. possibility of use as a medicament;
not substantially prevented, i.e. retarded or reduced, reaction with acidic gastric juice.

The present invention relates to antacid preparations having a long gastric residence time, characterized in that they contain antacid active compounds which are agglomerated with the calcium salt of polycarbophil using water-insoluble anionic polymers as binders, and as a result have a high adhesion (bioadhesion) to the gastric mucosa and a prolonged gastric passage.

This effect is surprising insofar as a retarding influence of calcium polycarbophil on the gastric passage was not to be expected. On the contrary, it was known that calcium polycarbophil does not influence the gastric residence time of barium preparations which are ingested before an X-ray examination (Current Therapeutic Research, 6, Pages 572 to 583, 1964).

The use of calcium polycarbophil as an agent against diarrhea and constipation (antidiarrheal and laxative) is also known, owing to the swelling and water-binding properties which the substance displays in the intestine. The present invention additionally unexpectedly shows that agglomeration of antacid active compounds with calcium polycarbophil using those water-insoluble anionic polymers whose customary field of application is the production of enteric-coated pharmaceutical preparations does not lead to a prolongation of the reaction of the antacid with hydrochloric acid. These polymers are customarily employed as enteric coatings in order to construct a protective shield against the attack of hydrochloric acid on the pharmaceutical or to protect the stomach from liberated active compound.

The invention relates in particular to preparations, such compressed by customary methods to give tablets (chewable tablets, dispersible tablets, coated tablets) or filled into capsules or sachets, comprising:

| a) | antacid active substance | 1 part by weight |
|---|---|---|
| b) | calcium polycarbophil | 0.1–5 parts by weight |
| c) | water-insoluble anionic polymer | 0.01–1 part by weight | and, if appropriate, additionally other customary auxiliaries and additives.

Particularly preferred preparations are those comprising:

| antacid active substance | 1 part by weight |
|---|---|
| calcium polycarbophil | 0.5–2 parts by weight |
| water-insoluble anionic polymer | 0.1–0.5 part by weight |

All customary active compounds having acid-binding or neutralizing properties can be employed as the antacid active substance.

Aluminum and/or magnesium-containing antacids are preferably employed. Aluminum- and magnesium-containing antacids having a layer lattice structure, such as, for example, hydrotalcite, magaldrate and almagate are particularly preferred.

Calcium polycarbophil is known [U.S. Pharmacopoeia (USP XXII)] as the calcium salt of a polyacrylic acid which is crosslinked with divinyl glycol. The substance is marketed by Goodrich under the trade names "Carbopol EX83" and "Carbopol 977". "Carbopol 977" is particularly highly suitable owing to its small particle size (below 15 μm) for use in chewable tablets an dispersable tablets and is preferably employed in the agglomerates according to the invention.

Water-insoluble, anionic polymers which are preferably their use as polymers producing gastric juice resistance, such as, for example polyacrylic acid/methacrylate copolymer
cellulose acetate phthalate
hydroxypropylmethylcellulose phthalate
cellulose acetate succinate
cellulose acetate adipate
shellac
polyvinyl acetate phthalate
cellulose acetate trimellitate
hydroxypropyl methylcellulose acetate succinate Polyacrylic acid/methacrylate copolymer is particularly preferably employed. This substance is marketed under the trade name "Eudragit L 100-55" or in the form of a 30% strength aqueous dispersion under the name "Eudragit L 30 D" by Röhm, Darmstadt. It is described in the American "National Formulary, NF XVII" under the name "methacrylic acid copolymer" as "Type C".

The preparation according to the invention is prepared by customary methods such as agglomeration of the three components a, b and c using customary agglomeration techniques, such as moist granulation in mixers or fluidized bed equipment, dry granulation, extrusion, formation of spheres and pelletization.

The antacid agglomerates according to the invention display their gastric mucosa-adhering and rapidly neutralizing action best if they have an average particle size range of 55 to 2000 μm. Average particle sizes of 100 to 800 μm are particularly preferred.

Other pharmaceutical auxiliaries such as fillers, binders, plasticizers or disintegration auxiliaries can also be incorporated into the agglomerates. Pharmaceutically customary additives, such as are used in tablets, capsules or sachets, can furthermore also be admixed to the agglomerates. Additives of this type are, for example, fillers, binders, lubricants, flow-regulating agents, disintegration auxiliaries (tablet disintegrants), sweeteners based on carbohydrates, artificial sweeteners, sugar replacements and flavorings.

If the antacid-containing agglomerates according to the invention are further processed to give tablets, it is to be noted that these easily disintegrate on contact with aqueous medium as a result of the effect of tablet disintegrants in order to facilitate free distribution of the agglomerates on the gastric mucosa. The tablets should be designed as chewable tablets or as easily water-dispersible tablets.

The advantageous properties of the antacid preparations according to the invention ca be demonstrated by determination of the antacid activity (in vitro method) and the adhesive properties to pieces of excised dog's stomach.

(A) Antacid activity 150 ml of 0.1 N hydrochloric acid are warmed at 37° C. and stirred in a 300 ml beaker containing a magnetic stirrer (200 rpm). A glass electrode is introduced to measure the pH. A tablet formulation according to the invention (Example 1) is added to the hydrochloric acid initially introduced and the pH is recorded continuously by means of a recorder. 10 ml of 0.1 N hydrochloric acid are added dropwise after 10 minutes and in each case continuously after a further 10 minutes. The secretion of the stomach is simulated by this means.

The period over which the antacid is able to keep the pH of the system in the optimum pH range between 3 and 5 is determined. The test furthermore makes it possible to distinguish whether the antacid rapidly neutralizes the additional supply of 10 ml of 0.1 N hydrochloric acid or whether a long-lasting decrease in the pH results.

FIG. 1 shows the results of the antacid activity test for the tablet formulation according to Example 1.

(B) Investigation of the adhesive properties to excised pieces of dog's stomach

A simple model was developed in order to determine the adhesive properties of antacid preparations to dog gastric mucosa. The gastric mucosa of the dog is essentially comparable to that of the human. Round pieces having a diameter of about 5 cm are taken from the stomach of a sacrificed dog. These pieces are tensioned in a holder which makes the inner surface of the stomach and thus the mucosa accessible for subsequent investigations. An aqueous suspension of the antacid preparations according to the invention is painted onto the surface of the gastric mucosa and the entire holder is suspended in a beaker containing 0,1 N hydrochloric acid at 37° C. and the beaker is vigorously stirred. The adhesion of the preparation to the mucosal surface is monitored optically over a relatively long period of, for example, 90 min.

While adhesion to the mucosa can only be detected for at most 10 minutes with Talcid ® tablets and other commercial antacid preparations, a strong adhesion can still be detected with the preparation according to the invention even after 90 minutes.

EXAMPLE 1

Tablets containing 1 g of hydrotalcite and having a prolonged gastric residence time

| | |
|---|---|
| Hydrotalcite | 1,000 mg |
| Polyacrylic acid/methacrylate copolymer (employed as 30% strength Eudragit L 30 D ® dispersion) | 225 mg |
| Polyvinylpyrrolidone 25 | 50 mg |
| 1,2-Propylene glycol | 100 mg |
| Calcium polycarbophil | 1,000 mg |
| Crospovidone | 343 mg |
| Highly disperse silica | 50 mg |
| Saccharin sodium | 10 mg |
| Banana flavouring | 2 mg |
| Calcium stearate | 20 mg |

10 kg of hydrotalcite are weighed into a mixing granulator. A granulation liquid is additionally prepared by dissolving 0.5 kg of polyvinylpyrrolidone 25 and 1 kg of 1,2-propylene glycol in 7.5 kg of Eudragit L 30 D dispersion. The granulation liquid is added to the hydrotalcite in the mixing granulator with stirring, moist granules being formed. 10 kg of calcium polycarbophil are added to these moist granules and the mixture is vigorously additionally stirred. The granules are grated, dried and then screened through a sieve of internal mesh width 1 mm. 3.43 kg of crospovidone, 0.5 kg of highly disperse silica, 0.1 kg of saccharin sodium, 20 g of banana flavouring and 0.2 kg of calcium stearate are admixed to the screened granules. The made-up mixture is compressed in a revolving tablet press to give tablets having a weight of 2.8 g and a diameter of 25 mm.

The tablets obtained disintegrate in water at 37° C. in less than two minutes and liberate hydrotalcite-containing granule particles having high adhesive power to the gastric mucosa.

EXAMPLE 2

800 mg of magaldrate-containing tablets having prolonged gastric residence time

| | |
|---|---|
| Magaldrate | 800 mg |
| Cellulose acetate phthalate (employed as a 20% strength Aquateric ® dispersion) | 180 mg |
| Polyvinylpyrrolidone/polyvinyl acetate copolymer | 30 mg |
| Triacetin | 40 mg |
| Calcium polycarbophil | 800 mg |
| Sodium carboxymethyl starch | 200 mg |
| Highly disperse silica | 30 mg |
| Xylitol | 300 mg |
| Saccharin sodum | 5 mg |

-continued

| | |
|---|---|
| Peppermint flavoring | 5 mg |
| Magnesium stearate | 10 mg |

8 kg of magaldrate are weighed into a mixing granulator.

A granulation liquid is prepared by dissolving 0.3 kg of polyvinylpyrrolidone/polyvinyl acetate copolymer and 0.4 kg of triacetin in 9 kg of Aquateric ® dispersion. The granulation liquid is added to the magaldrate in the mixing granulator with stirring, moist granules being formed. 8 kg of calcium polycarbophil and 1 kg of sodium carboxymethyl starch are added to these moist granules and the mixture is vigorously additionally stirred. The granules are grated, dried and subsequently screened through a sieve of internal mesh width 1 mm. 1 kg of sodium carboxymethyl starch, 0.3 kg of highly disperse silica, 3 kg of xylitol, 50 g of saccharin sodium, 50 g of peppermint,-flavoring and 0.1 kg of magnesium stearate are admixed to the screened granules. The made-up mixture is compressed in a revolving tablet press to give tablets having a weight of 2.4 g and a diameter of 22 mm.

EXAMPLE 3

| | |
|---|---|
| Aluminium hydroxide/magnesium hydroxide co-dried gel | 800 mg |
| Hydroxypropylmethylcellulose phthalate | 150 mg |
| Polyethylene glycol 6000 | 50 mg |
| Crospovidone | 170 mg |
| Calcium polycarbophil | 1,000 mg |
| Mannitol | 300 mg |
| Saccharin sodium | 5 mg |
| Peppermint flavoring | 5 mg |
| Calcium stearate | 20 mg |

Preparation is carried out analogously to Examples 1 and 2. One difference is that hydroxypropylmethylcellulose phthalate is not processed from an aqueous dispersion, but from an alcoholic solution.

The tablets obtained having a weight of 2.5 g and a diameter of 22 mm disintegrate in water into particles having good adhesion to the gastric mucosa.

We claim:

1. Antacid preparations having a prolonged gastric residence time, comprising antacid active compounds which are agglomerated with the calcium salt of polycarbophil using water-insoluble anionic polymers as binders, have a high adhesion (bioadhesion) to the gastric mucosa and as a result have a prolonged gastric passage.

2. Antacid preparations according to claim 1, comprising 1 part by weight of antacid active compound, 0.1 to 5 parts by weight of calcium polycarbophil, 0.01 to 1 part by weight of water-insoluble anionic polymer and, if appropriate, additionally other customary auxiliaries and additives.

3. Antacid preparations according to claim 1 containing 0.1 to 0.5 parts by weight of water-insoluble anionic polymer.

4. Antacid preparations according to claim 1 containing antacid active compounds which contain aluminium and/or magnesium and have layer lattice structure.

5. Antacid preparations according to claim 1 containing hydrotalcite, magaldrate or almagate as active compounds.

6. Antacid preparations containing calcium polycarbophil having an average particle size up to 15 $\mu$m.

7. Antacid preparations containing a compound from the group comprising polyacrylic acid/methacrylate copolymer, cellulose acetate phthalate, hydroxypropylmethylcellulose phthalate, cellulose acetate succinate, cellulose acetate adipate and/or shellac as water-insoluble anionic polymers.

8. Antacid preparations according to claim 1, wherein the antacid agglomerates have a mean particle size range of 25 to 2000 $\mu$m.

9. Process for the production of antacid preparations according to claim 1, wherein the three components a) antacid active substance, b) calcium polycarbophil and c) water-insoluble anionic polymer are agglomerated using customary agglomeration techniques such as moist granulation in mixers or fluidized bed equipment, dry granulation, extrusion, formation of spheres and pelletization and the agglomerates obtained are optionally converted into a suitable administration form using customary auxiliaries and excipients.

* * * * *